US012616370B2

(12) United States Patent
Abdolmanafi et al.

(10) Patent No.: US 12,616,370 B2
(45) Date of Patent: May 5, 2026

(54) SYSTEM AND METHOD FOR DETERMINING ATHEROSCLEROTIC PATHOLOGICAL TISSUE TYPES IN A CORONARY ARTERY OCT IMAGE USING TRAINED ENGINES

(71) Applicants: ECOLE DE TECHNOLOGIE SUPERIEURE, Montreal (CA); Nagib Dahdah, Ville Mont-Royal (CA); Ragui Ibrahim, Longueuil (CA)

(72) Inventors: Atefeh Abdolmanafi, Newmarket (CA); Luc Duong, Verdun (CA); Nagib Dahdah, Ville Mont-Royal (CA); Ragui Ibrahim, Longueuil (CA)

(73) Assignee: L'ÉCOLE DE TECHNOLOGIE SUPERIEURE, Montreal (CA)

( * ) Notice: Subject to any disclaimer, the term of this patent is extended or adjusted under 35 U.S.C. 154(b) by 451 days.

(21) Appl. No.: 18/247,892

(22) PCT Filed: Oct. 5, 2021

(86) PCT No.: PCT/CA2021/051389
§ 371 (c)(1),
(2) Date: Apr. 5, 2023

(87) PCT Pub. No.: WO2022/073109
PCT Pub. Date: Apr. 14, 2022

(65) Prior Publication Data
US 2023/0371816 A1      Nov. 23, 2023

Related U.S. Application Data

(60) Provisional application No. 63/087,495, filed on Oct. 5, 2020.

(51) Int. Cl.
*A61B 5/00*        (2006.01)
*G06T 7/00*        (2017.01)
(Continued)

(52) U.S. Cl.
CPC .......... *A61B 5/0066* (2013.01); *G06T 7/0012* (2013.01); *G06V 10/25* (2022.01);
(Continued)

(58) Field of Classification Search
CPC ...... A61B 5/0066; G16H 30/20; G16H 50/20; G06V 10/25; G06T 7/0012; G06T 2207/30101; G06T 7/11
(Continued)

(56) References Cited

U.S. PATENT DOCUMENTS 10,483,006 B2      11/2019   Itu et al.
2003/0028100 A1      2/2003   Tearney et al.
(Continued)

FOREIGN PATENT DOCUMENTS

CN        108052909        5/2018
CN        109091167        12/2018
(Continued)

OTHER PUBLICATIONS

Yu, Fisher & Koltun, Vladlen. (2016). Multi-Scale Context Aggregation by Dilated Convolutions.
(Continued)

*Primary Examiner* — Ming Shui
(74) *Attorney, Agent, or Firm* — Reno Lessard; Norton Rose Fulbright Canada LLP

(57)        ABSTRACT

There is described a system for determining an atherosclerotic pathological tissue type of a coronary artery, the system comprising: an optical coherence tomography (OCT) imaging system being configured for acquiring an OCT image of tissue within said coronary artery; and a controller configured for: using a trained fully convolutional engine stored on said memory and having a plurality of convolutional layers with respective dilation rates different than unity, extracting pathological tissues regardless their type in at least a region
(Continued)

of interest of said OCT image; using a trained auto-encoder classification engine stored on said memory and having a layer characterized with a sparsity regularization parameter, determining an atherosclerotic pathological tissue type associated to said region of interest of said OCT image based on said extracted pathological tissues; and outputting said atherosclerotic pathological tissue type of said coronary artery.

16 Claims, 12 Drawing Sheets

(51) Int. Cl.
  *G06V 10/25* (2022.01)
  *G16H 30/20* (2018.01)
  *G16H 50/20* (2018.01)
(52) U.S. Cl.
  CPC ............. *G16H 30/20* (2018.01); *G16H 50/20* (2018.01); *G06T 2207/10101* (2013.01); *G06T 2207/30101* (2013.01)
(58) Field of Classification Search
  USPC ................................................ 382/130, 128
  See application file for complete search history.

(56) References Cited

U.S. PATENT DOCUMENTS

| | | | |
|---|---|---|---|
| 2005/0251116 A1 | 11/2005 | Steinke et al. | |
| 2014/0119624 A1* | 5/2014 | Ethers et al. | ......... G06T 7/0012 |
| 2015/0121276 A1* | 4/2015 | Ryu et al. | .............. G16H 30/20 |
| 2016/0078309 A1 | 3/2016 | Feldman et al. | |
| 2017/0046839 A1 | 2/2017 | Paik et al. | |
| 2017/0251931 A1 | 9/2017 | Prakash et al. | |
| 2017/0309018 A1 | 10/2017 | Shalev et al. | |
| 2018/0055953 A1 | 3/2018 | Jaffer et al. | |
| 2018/0061049 A1* | 3/2018 | Robb et al. | |
| 2018/0214023 A1 | 8/2018 | Chen et al. | |
| 2019/0021598 A1 | 1/2019 | Eom | |
| 2020/0187790 A1 | 6/2020 | Milner et al. | |
| 2020/0226422 A1 | 7/2020 | Li et al. | |

FOREIGN PATENT DOCUMENTS

| | | | |
|---|---|---|---|
| RU | 2639861 | 12/2017 | |
| WO | WO 2014048573 A1 * | 9/2013 | ............. G16H 30/20 |
| WO | 2017214421 | 12/2017 | |

OTHER PUBLICATIONS

Abbasi, Ashkan & Monadjemi, Amirhassan & Fang, Leyuan & Rabbani, Hossein & Zhang, Yi. (2019). Three-dimensional optical coherence tomography image denoising through multi-input fully-convolutional networks.

* cited by examiner

Atrous conv.:
- Filter size: 3x3
- Parameters = 9
- Dilation rate = 2

Dilation

Standard conv.:
- Filter size: 3x3
- Parameters = 9

SYSTEM AND METHOD FOR DETERMINING ATHEROSCLEROTIC PATHOLOGICAL TISSUE TYPES IN A CORONARY ARTERY OCT IMAGE USING TRAINED ENGINES

FIELD

The improvements generally relate to the field of pathological tissue type determination in coronary artery optical coherence tomography (OCT) images, and more specifically involve computer-implemented engines trained using artificial intelligence.

BACKGROUND

OCT imaging techniques involve the use of coherent light which can penetrate well into coronary artery tissues, thus allowing not only an inside wall of the coronary artery to be imaged, but also allowing imaging of deeper layers of the coronary artery. Although existing OCT imaging techniques are satisfactory to a certain degree, there remains room for improvement. For instance, as acquiring a multitude of OCT images of coronary artery tissue of a patient can be relatively straightforward using existing OCT imaging systems, examining these OCT images can require a significant amount of time from highly qualified physicians.

SUMMARY

It is an aim of the present disclosure to describe methods and systems suited for determining pathological tissue type(s) associated with OCT images representing a coronary artery of a patient with atherosclerosis. The methods and systems involve the use of computer-implemented trained engines to extract pathological tissues regardless their types from a coronary artery OCT image. Then, the extracted pathological tissues are classified into respective atherosclerotic pathological tissue types. It was found that there was a need for computer-implemented trained engines which can perform the pathological tissue extraction and classification using raw, unprocessed OCT images of the coronary artery of the patient while still achieving satisfactory results. It is noted that the examples described herein have been used for determining and identifying atherosclerotic plaque tissue(s) in one or more regions of interest of a given coronary artery OCT image.

In accordance with a first aspect of the present disclosure, there is provided a system for determining an atherosclerotic pathological tissue type of a coronary artery, the system comprising: an OCT imaging system being configured for acquiring an OCT image of tissue within said coronary artery; and a controller having a processor and a memory having instructions stored thereon that when executed by said processor perform the steps of: using a trained fully convolutional engine stored on said memory and having a plurality of convolutional layers with respective dilation rates different than unity, extracting a plurality of pathological tissues regardless their type in at least a region of interest of said OCT image; using a trained auto-encoder classification engine stored on said memory and having a layer characterized with a sparsity regularization parameter, determining an atherosclerotic pathological tissue type associated to said region of interest of said OCT image based on said extracted pathological tissues; and outputting said atherosclerotic pathological tissue type of said coronary artery.

Further in accordance with the first aspect of the present disclosure, said atherosclerotic pathological tissue type can for example be selected from the group consisting of: fibrous plaque, fibrocalcific, fibroatheroma, acute thrombus, and micro-vessels.

Still further in accordance with the first aspect of the present disclosure, at least one of said dilation rates can for example be greater than a dilation rate threshold.

Still further in accordance with the first aspect of the present disclosure, said dilation rate threshold can for example be the unity.

Still further in accordance with the first aspect of the present disclosure, the layer of the auto-encoder classification engine can for example be a hidden layer.

Still further in accordance with the first aspect of the present disclosure, said sparsity regularization parameter can for example range within a given sparsity regularization parameter range.

Still further in accordance with the first aspect of the present disclosure, said outputting can for example include generating an output image having the atherosclerotic pathological tissue type overlaid over said OCT image, with a lead line leading to the region of interest.

Still further in accordance with the first aspect of the present disclosure, upon finding at least one atherosclerotic pathological tissue type in said OCT image, the method can for example include a step of associating a tag indicative of unhealthiness to the OCT image.

In accordance with a second aspect of the present disclosure, there is provided a method for determining an atherosclerotic pathological tissue type of a coronary artery, the method comprising: using an OCT imaging system, acquiring an OCT image of tissue within said coronary artery; using a controller, using a trained fully convolutional engine stored on a memory of said controller and having a plurality of convolutional layers with respective dilation rates, extracting a plurality of pathological tissues regardless their types in at least a region of interest of said OCT image; using a trained auto-encoder classification engine stored on said memory and having a layer characterized with a sparsity regularization parameter, determining an atherosclerotic pathological tissue type associated to said region of interest of said OCT image based on said extracted pathological tissues; and outputting said atherosclerotic pathological tissue type of said coronary artery.

Further in accordance with the second aspect of the present disclosure, said atherosclerotic pathological tissue type can for example be selected from the group consisting of: fibrous plaque, fibrocalcific, fibroatheroma, acute thrombus, and micro-vessels.

Still further in accordance with the second aspect of the present disclosure, at least one of said dilation rates can for example be greater than a dilation rate threshold.

Still further in accordance with the second aspect of the present disclosure, said dilation rate threshold can for example be the unity.

Still further in accordance with the second aspect of the present disclosure, the layer of the auto-encoder classification engine can for example be a hidden layer.

Still further in accordance with the second aspect of the present disclosure, said sparsity regularization parameter can for example range within a given sparsity regularization parameter range.

Still further in accordance with the second aspect of the present disclosure, said outputting can for example include generating an output image having the atherosclerotic pathological tissue type overlaid over said OCT image, with a lead line leading to the region of interest.

Still further in accordance with the second aspect of the present disclosure, upon finding at least one atherosclerotic pathological tissue type in said OCT image, the method can for example include a step of associating a tag indicative of unhealthiness to the OCT image.

Many further features and combinations thereof concerning the present improvements will appear to those skilled in the art following a reading of the instant disclosure.

DESCRIPTION OF THE FIGURES

In the figures.

DETAILED DESCRIPTION

The systems and methods described herein are used for the determination of one or more pathological tissue types in one or more regions of interest in a coronary artery OCT image. In some embodiments, the pathological tissue type can be an atherosclerotic plaque tissue type such as fibrous plaque, fibrocalcific, fibroatheroma, acute thrombus, and micro-vessels, and/or any other suitable types of coronary artery pathological tissue.

Figure 1:
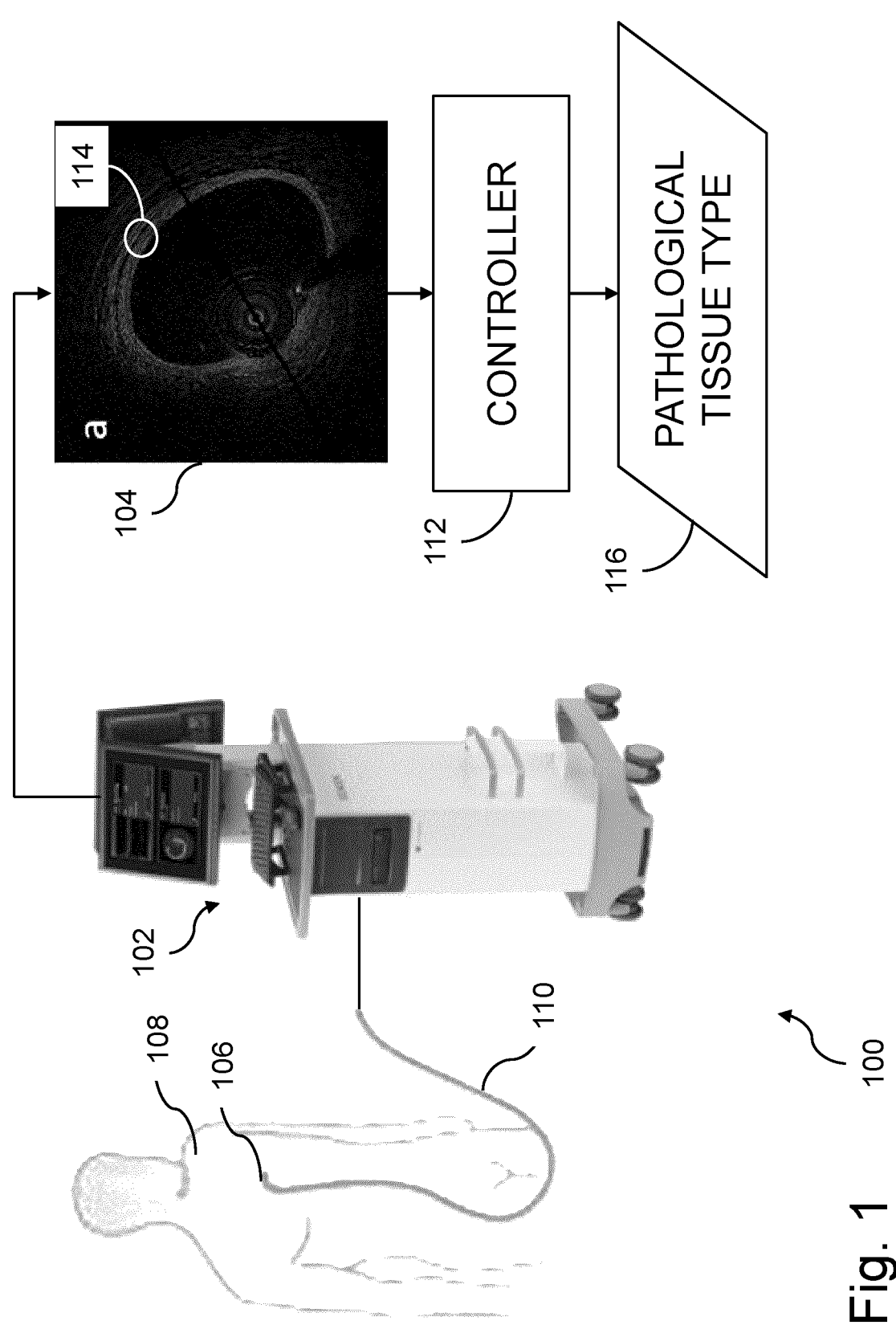
FIG. 1 is a schematic view of an example of a system for determining a pathological tissue type in a coronary artery OCT image, showing an OCT system and a controller, in accordance with one or more embodiments.

FIG. 1 illustrates an example of a system 100 for determining a pathological tissue type in a coronary artery, in accordance with one or more embodiments. As depicted, the system has an OCT imaging system 102. As shown, the OCT imaging system 102 is configured for acquiring an OCT image 104 of coronary artery tissue 106 of a patient 108 (referred to as "coronary artery OCT image 104" hereinafter).

Generally, the OCT imaging system 102 has an optical source which is configured to emit an optical signal to be propagated along a waveguide of a guide wire 110 leading to a probe, and an optical detector which is configured to receive a return optical signal from the probe. During use, the probe and a portion of the guide wire 110 are inserted into the coronary artery 106 of the patient 108 for acquiring coronary artery OCT images 104. The coronary artery OCT images 104 can be stored and/or processed within a controller 112 of the OCT imaging system 102 in some embodiments. The controller 112 can have a processing unit, and a non-transitory computer-readable memory communicatively coupled to the processing unit and comprising computer-readable program instructions executable by the processing unit for determining a coronary artery pathological tissue type.

In this specific example, the OCT imaging system 102 is provided in the form of the ILUMIEN OCT imaging system (St. Jude Medical Inc., St. Paul, Minnesota, USA). More specifically, the OCT imaging system 102 has axial and lateral resolutions of 12-15 µm and 20-40 µm, respectively. According to a non-limitative embodiment, OCT image acquisition is performed using frequency domain (FD) OCT with pullback speed of 20 mm/sec and frame rate of 1000 frames/sec. However, depending on the embodiment, any other suitable OCT imaging system can be used.

As shown, the controller 112 is communicatively coupled to the OCT imaging system 102. The communication between the controller 112 and the OCT imaging system 102 can be wired and/or wireless, depending on the embodiment.

As will be described in greater detail below, once a coronary artery OCT image 104 is acquired by the OCT imaging system 102, the controller 112 is configured for extracting pathological tissues regardless their types in at least a region of interest 114 of the coronary artery OCT image 104, using at least a previously trained fully convolutional engine. The fully convolutional engine has one or more convolutional layers with respective dilation rates different than the unity, i.e., different than one. Accordingly, the convolutional layers used in the fully convolutional engine are dilated convolutional layers. The controller 112 then determines a pathological tissue type associated with the region of interest 114 of the coronary artery OCT image 104 based on the pathological tissues using a trained auto-encoder classification engine stored on a memory of the controller 112. The auto-encoder classification engine generally has at least an input layer, a hidden layer and an output layer, with the hidden layer having a sparsity regularization parameter ensuring that the auto-encoder is sparse. Once the atherosclerotic pathological tissue type 116 of the coronary artery has been determined, the controller 112 can generate a signal indicative of the atherosclerotic pathological tissue type 116 for further use. It was found that the combination of the above-described fully convolutional engine and auto-encoder classification engine was conveniently disposed for processing raw, unprocessed coronary artery OCT images in the context of pathological tissue determination.

The controller 112 can be provided as a combination of hardware and software components. The hardware components can be implemented in the form of a computing device 200, an example of which is described with reference to FIG. 2. Moreover, the software components of the controller 112 can be implemented in the form of a software application 300, an example of which is described with reference to FIG. 3.

Figure 2:
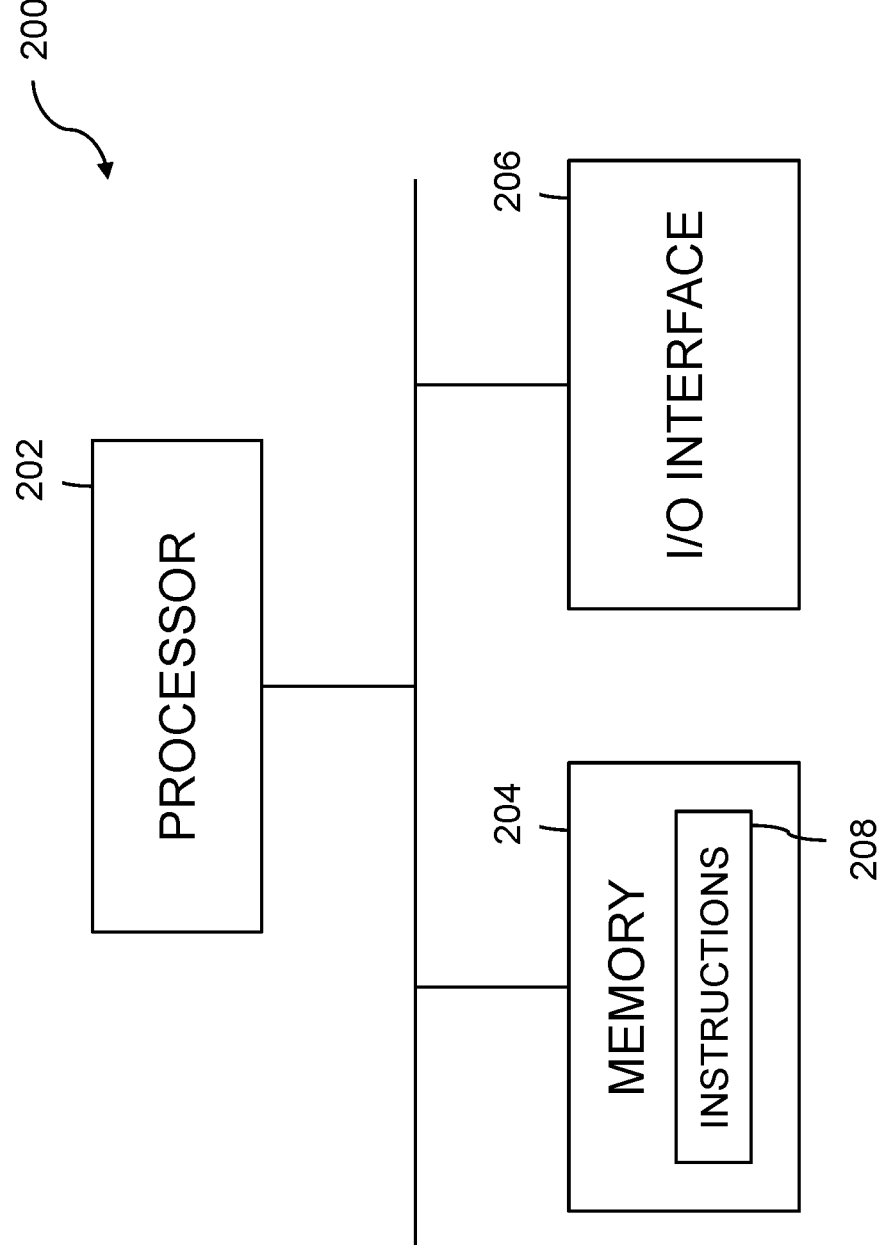
FIG. 2 is a schematic view of an example of a computing device of the controller of FIG. 1, in accordance with one or more embodiments.

Turning now to FIG. 2, the computing device 200 has a processor 202, a memory 204, and an I/O interface 206. Instructions 208 for determining the pathological tissue type can be stored on the memory 204 and accessible by the processor 202.

The processor 202 can be, for example, a general-purpose microprocessor or microcontroller, a digital signal processing (DSP) processor, an integrated circuit, a field programmable gate array (FPGA), a reconfigurable processor, a programmable read-only memory (PROM), or any combination thereof.

The memory 204 can include a suitable combination of any type of computer-readable memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 206 enables the computing device 200 to interconnect with one or more input devices, such as the OCT imaging system 102, or with one or more output devices such as a monitor, a mobile electronic device, a database, an external network and the like.

Each I/O interface 206 enables the controller 112 to communicate with other components, to exchange data with other components, to access and connect to network resources, to server applications, and to perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

Figure 3:
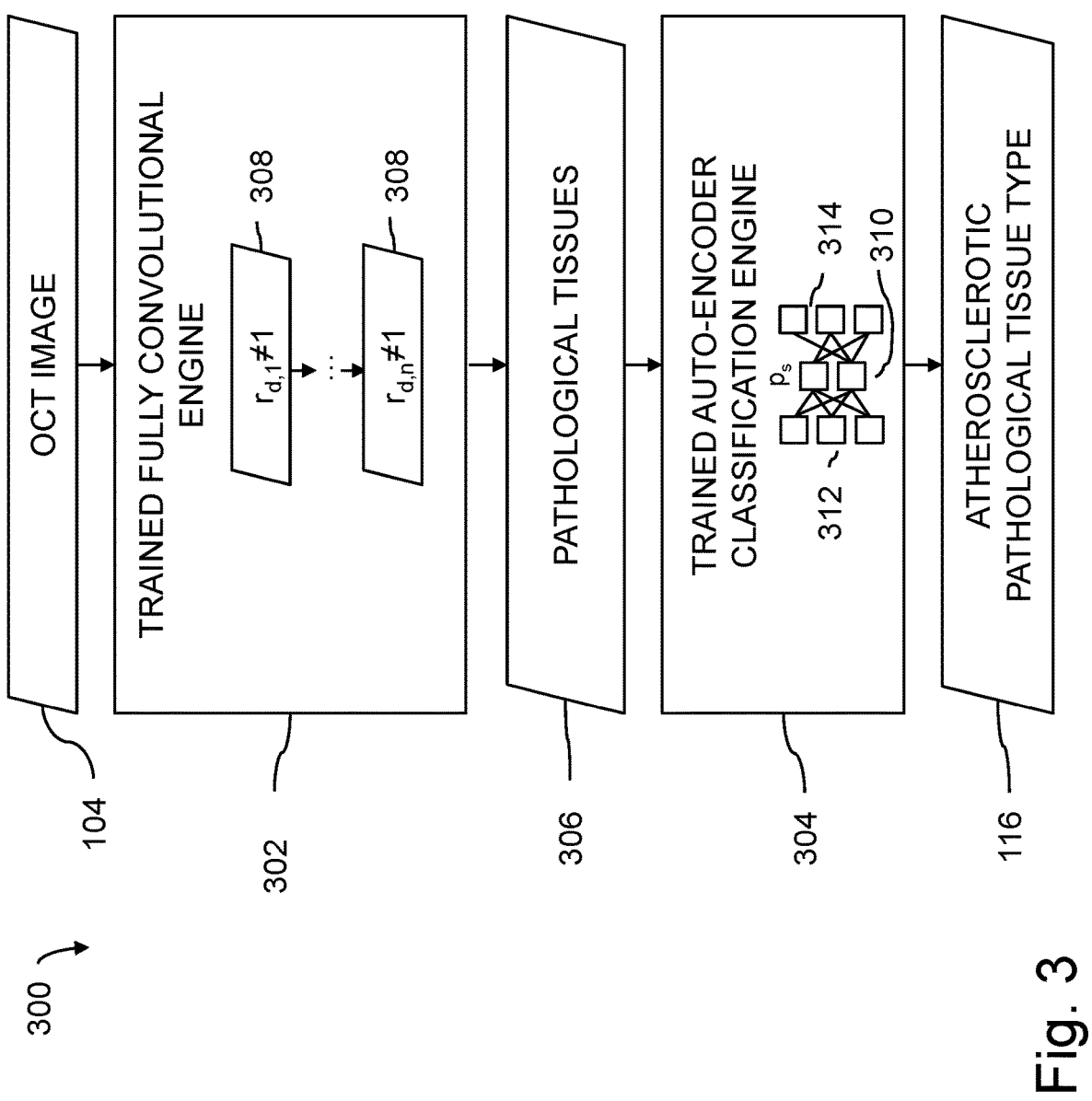
FIG. 3 is a schematic view of an example of a software application of the controller of FIG. 1, in accordance with one or more embodiments.

Referring to FIG. 3, the software application 300 is configured to receive the coronary artery OCT image 104 and to determine the atherosclerotic pathological tissue type 116 associated to the region of interest 114 of the coronary artery OCT image 104 upon processing the coronary artery OCT image 104. In some embodiments, the software application 300 is stored on the memory 204 and accessible by the processor 202 of the computing device 200. In the example described in the following paragraphs, the software application 300 is provided in the form of non-transitory computer-readable program instructions that can be executed by the controller 112. Description of the software application 300 is made with reference to the system 100 of FIG. 1 for ease of reading.

As shown, the software application 300 has a trained fully convolutional engine 302 and a trained auto-encoder classification engine 304 working synergistically with one another to output one or more atherosclerotic pathological tissue types 116 on the basis of one or more coronary artery OCT images 104. This combination results in accelerating the analysis of atherosclerotic OCT images by minimizing the computational complexity and accelerating the model performance by using original images without pre-processing, and advantages of using dilated convolutions. Using the advantages of deep features and sparse autoencoder to generate more features and expanding on the training data, as well as using sparse autoencoder for plaque type characterization with fast and accurate training using minimum feature extraction process are the other advantages of proposed technique. The proposed software system can detect atherosclerotic pathological tissues in adult population, which are completely different from pathological tissues in Kawasaki disease in children. In current software system, only one set of features extracted from pathological tissues using a CNN were used along with an auto-encoder to analyze the extracted features and take the classification decision to discriminate between various atherosclerotic pathological tissue types without the need of using majority voting and other computationally cumbersome engines.

More specifically, the fully convolutional engine 302 has one or more convolutional layers 308 with dilation rates $r_d$ different than unity, i.e., different than one. As such, the fully convolutional engine 302 can extract a plurality of pathological tissues 306 in at least a region of interest of the coronary artery OCT image 104. In some embodiments, the dilation rate $r_d$ of the convolutional layer is greater than a dilation rate threshold $r_{d,thres}$, i.e., $r_d > r_{d,thres}$. In these embodiments, the dilation rate threshold is the unity. Accordingly, the dilation rate $r_d$ is greater than one, i.e., $r_d > 1$. However, in some other embodiments, the dilation rate threshold $r_{d,thres}$ may be greater than one.

As shown in the illustrated example, the auto-encoder classification engine 304 is configured to determine an atherosclerotic pathological tissue type 116 associated to the region of interest of the coronary artery OCT image 104 based on the pathological tissues 306 determined by a CNN. As shown, the auto-encoder classification engine 304 has a layer 310 characterized with a sparsity regularization parameter $p_s$. As depicted, the auto-encoder classification engine 304 has a number of input layers 312, a number of hidden layer 310, and a number of output layers 314. In this embodiment, the sparsity regularization parameter $p_s$ characterizes the hidden layer 310 thereby ensuring that the auto-encoder classification engine 304 is a sparse auto-encoder classification engine. More specifically, the sparsity regularization parameter $p_s$ can be referred to as a penalty term, which is used in the loss function to enforce a constraint on the sparsity of the output from the hidden layer. It is noted that in some embodiments, the sparsity regularization parameter $p_s$ ranges within a given sparsity regularization parameter range $[p_{s,min}; p_{s,max}]$. The sparsity regularization parameter range can vary from one embodiment to another.

Figures 4A, 4B, 5:
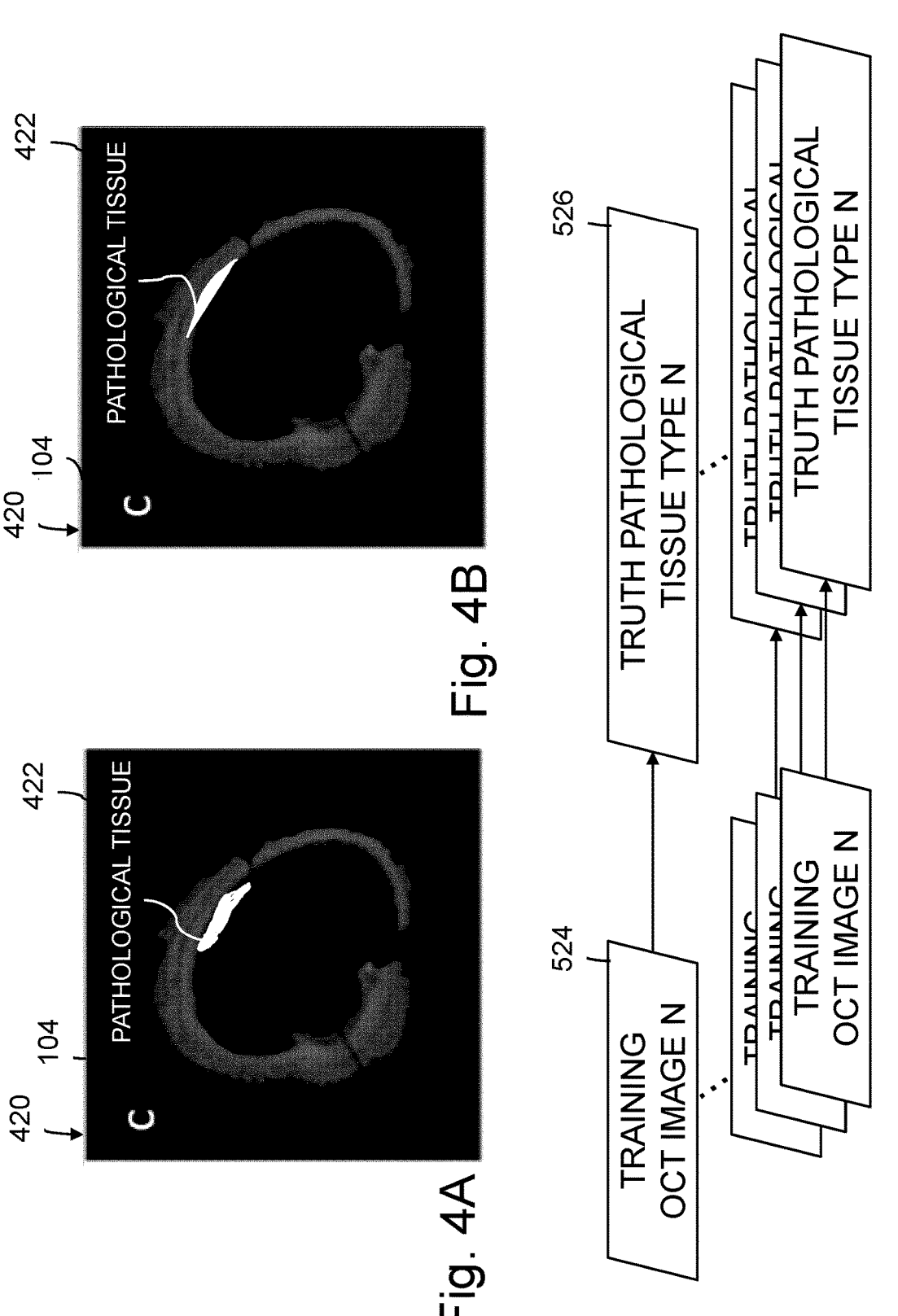
FIG. 4A is an example of an output of the system of FIG. 1, showing an OCT image with an overlaid text string indicative of a first pathological tissue type of a region of interest of the OCT image, in accordance with one or more embodiments.
FIG. 4B is an example of an output of the system of FIG. 1, showing an OCT image with an overlaid text string indicative of a second pathological tissue type of another region of interest of the OCT image, in accordance with one or more embodiments.
FIG. 5 is a schematic view of exemplary training OCT images and associated truth pathological tissue types, in accordance with one or more embodiments.

In some embodiments, the auto-encoder classification engine 304 can be configured to overlay an output indicating the atherosclerotic pathological tissue type 116 on the coronary artery OCT image 104. For instance, in these embodiments, the output can include at least a text string overlaid on the coronary artery OCT image 104. The text string can be indicative of the determined atherosclerotic pathological tissue type 116. As such, FIG. 4A shows a coronary artery OCT image 104 onto which a text string 422 indicating a first pathological tissue type has been overlaid. Similarly, FIG. 4B shows a coronary artery OCT image 104 onto which a text string 422 indicating a second pathological tissue type of the coronary artery has been overlaid.

As can be understood, in this example, the fully convolutional and auto-encoder classification engines 302 and 304 have been trained using supervised learning during which the engines 302 and 304 are trained to extract relevant pathological tissues and to determine a pathological tissue type in a plurality of training coronary artery OCT images each showing different coronary artery pathological tissue types and having truth tissue type associated to each of the training coronary artery OCT images. Example of training OCT images 524 and their associated truth tissue type 526 are shown in FIG. 5.

The computing device 200 and the software application 300 described above are meant to be examples only. Other suitable embodiments of the controller 112 can also be provided, as it will be apparent to the skilled reader.

Figure 6:
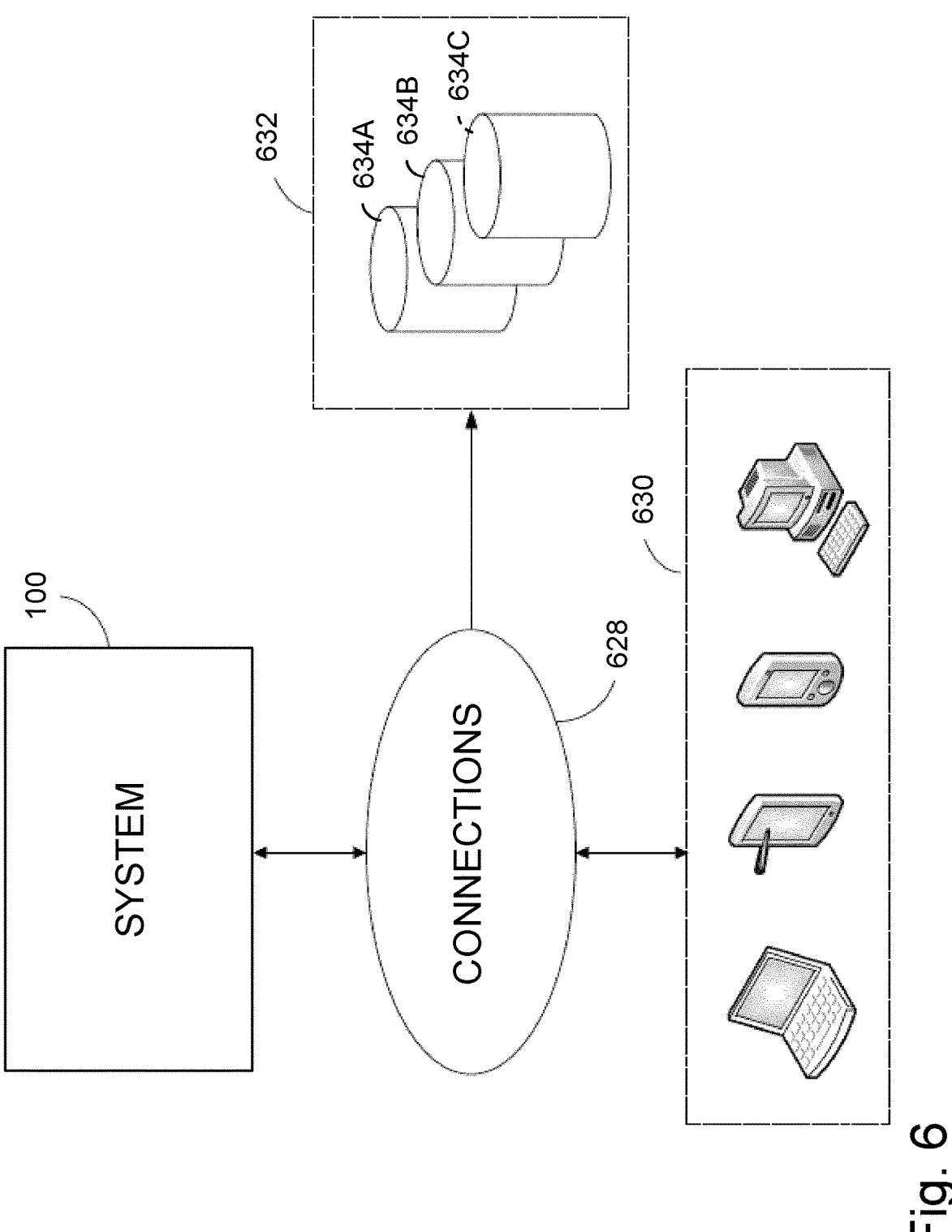
FIG. 6 is a block diagram illustrating an exemplary system incorporating the system of FIG. 1 via network(s) and connection(s), in accordance with one or more embodiments.

Referring now to FIG. 6, in some embodiments, the system 100 may be accessible remotely from any one of a plurality of external devices 630 over connections 628. External devices 630 may be any one of a desktop, a laptop, a tablet, a smartphone, and the like. External devices 630 may have a software application such as software application 300 of FIG. 3 provided wholly or partly thereon as a downloaded software application, a firmware application, or a combination thereof, for accessing the system 100 of FIG. 1. Alternatively, external devices 630 may access the system 100 of FIG. 1 via a web application, accessible through any type of Web browser.

The connections 628 may comprise wire-based technology, such as electrical wires or cables, and/or optical fibers. The connections 628 may also be wireless, such as RF, infrared, Wi-Fi, Bluetooth, and others. The connections 628 may therefore comprise a network, such as the Internet, the Public Switch Telephone Network (PSTN), a cellular network, or others known to those skilled in the art. Communication over the network may occur using any known communication protocols that enable external devices 630 within a computer network to exchange information. The examples of protocols are as follows: IP (Internet Protocol), UDP (User Datagram Protocol), TCP (Transmission Control Protocol), DHCP (Dynamic Host Configuration Protocol), HTTP (Hypertext Transfer Protocol), FTP (File Transfer Protocol), Telnet (Telnet Remote Protocol), SSH (Secure Shell Remote Protocol).

In some embodiments, the software application 300 of FIG. 3 is provided at least in part on any one of external devices 630. For example, the software application 300 may be configured as a first portion provided in the system 100 of FIG. 1 to obtain and transmit the inputs such as the pathological tissues to a second portion, provided on one of the external devices 630. The second portion may be configured to receive the inputs such as the coronary artery OCT image(s) 104 and/or the pathological tissues, and perform the steps carried by the auto-encoder classification engine 304 on one of the external devices 630. Alternatively, the software application 300 is provided entirely on any one of the external devices 630 and is configured to receive a coronary artery OCT image 104 from a remote OCT imaging system. Also alternatively, the system 100 of FIG. 1 can be configured to transmit, via connections 628, one or more of inputs such as the coronary artery OCT image(s) 104, the pathological tissues, and/or the atherosclerotic pathological tissue types(s) 116. Other embodiments may also apply.

One or more databases 632, such as databases 634A, 634B and/or 634C may be provided locally on any one of the system 100 of FIG. 1 and the external devices 630, or may be provided separately therefrom (as illustrated). In the case of a remote access to the databases 632, access may occur via the connections 628 taking the form of any type of network, as indicated above. The various databases 632 described herein may be provided as collections of data or information organized for rapid search and retrieval by a computer. The databases 632 may be structured to facilitate storage, retrieval, modification, and deletion of data in conjunction with various data-processing operations. The databases 632 may be any organization of data on a data storage medium, such as one or more servers. The databases 632 illustratively have stored therein raw data representing training coronary artery OCT images 524 and associated truth pathological tissue type 526.

Each software application described herein may be implemented in a high-level procedural or object-oriented programming or scripting language, or a combination thereof, to communicate with a computer system. Alternatively, the software applications may be implemented in assembly or machine language. The language may be a compiled or interpreted language. Computer-executable instructions may be in many forms, including program modules, executed by one or more computers or other devices. Generally, program modules include routines, programs, objects, components, data structures, etc., that perform tasks or implement particular abstract data types. Typically, the functionality of the program modules may be combined or distributed as desired in various embodiments.

Example—Atherosclerotic Plaque Characterization in Coronary Artery Using OCT Imaging Coronary artery disease (CAD) is associated with coronary atherosclerosis, which is the main leading cause of myocardial infarction with almost seven million reported deaths worldwide. Understanding the process of plaque development, progression, and rupture is significant to guide enhancing the existing techniques for better indication of plaque morphology and improving patient's outcome. Catheter-based procedures, minimally invasive interventional methods, are prime in assisting millions of patients every year. Open heart surgery for coronary bypass intervention is therefore often avoided. Catheter-based procedures still require better understanding the type and location of coronary plaques in order to personalize treatment and target the most vulnerable lesions.

Accumulation of Low-Density Lipoprotein (LDL) results in a lipid-driven coronary inflammatory called atherosclerosis. Normal arterial wall is a three-layered structure. Intima is the first arterial wall layer surrounded by endothelial cells. The second layer, media, is responsible to provide bio-mechanical strength of the artery and control the reversible extensibility of the arterial wall during cardiac cycles. Media is composed of Smooth Muscle Cells (SMCs) and Extracellular Matrix (ECM), which is separated from intima, and the third layer, adventitia, with internal and external elastic lamina respectively. Endothelial cells provide anti-thrombotic molecules to prevent blood clot. In addition, they adjust contraction of the SMCs in Media. The inflammatory process in atherosclerosis starts with endothelial dysfunction, and accumulation of lipids in intima layer and continues by infiltration of SMCs and accumulation of macrophages to form foam cells. Progression of atherosclerotic lesions results in development of various plaque profiles including fibrous plaque, fibrocalcific plaque, fibroatheroma, and lesions with acute thrombosis. The earliest stage of atherosclerotic plaque development is called pathological intimal thickening or fibrous plaque. Fibrous plaque is intimal thickening followed by small area of lipid pool and possible macrophage accumulation. Micro-calcification and cholesterol crystals can be seen in fibrous plaques. Lack of enough oxygen in intimal thickening results in formation of micro-vessels with permeable and weak structure. Micro-vessels can be the sign of plaque instability since they cause infiltration of lipids and inflammatory cells into the intima layer and followed by intraplaque haemorrhage. Intimal calcification is the most common form of fibrocalcific plaques with the lowest grade formation in fibrous plaque and the highest-grade formation in fibroatheroma. Calcification is a sign of plaque stability since calcified arterial wall tissues are hard to get ruptured. Progressive atherosclerosis is recognized by fibroatheroma development. Degrading the collagen and infiltration of SMCs results in reducing the fibrous cap thickness and remodelling of the arterial wall. Invasion of macrophages to act as mediators results in necrotic core formation. Extensive lipid pool/necrotic core and macrophage infiltration are the most common characteristics of fibroatheroma. Extensive macrophage infiltration results in plaque rupture. This leads to coronary thrombosis and acute coronary syndrome.

Coronary angiography (CA) is widely used in cardiology to evaluate structural variations of coronary artery in CAD. Using x-ray, intravascular structure can be evaluated if it becomes calcified. Moreover, the system is limited to determine intracoronary plaque sub-components due to its low spatial resolution of 0.5-0.7 mm. Indication of plaque morphology requires detailed information of tissues under review in cross-sectional view. Intravascular Ultrasound (IVUS) is a catheter-based imaging system, which provides gray-scale cross-sectional images of coronary artery with the resolution of 100-150 μm. IVUS is restricted to visualize plaque components due to its low spatial resolution. Virtual histology IVUS is still limited to indicate fibroatheroma, which is the most important determinant of plaque rupture. OCT is the state-of-the-art imaging system in atherosclerotic plaque indication. As discussed above, OCT employs interferometry using back-scattered near-infrared light to image intracoronary cross-sections with high resolution of 10-15 μm. Due to its high resolution, OCT can provide detailed information of intracoronary tissues including plaque morphology, and plaque sub-components. Fast image acquisition, and non-ionizing radiation are other advantages of using OCT. Despite the strengths, OCT has significant limitations to be addressed. Recent studies have evaluated inter-observer agreement in interpretation of OCT images. Based on this study, understanding the clinical features of various coronary plaques in OCT images can improve the inter-observer agreement in various degrees depending on the type of pathology. This improved interpretation comes following extensive focused training, and yet remains sub-optimal to general practice. This example thereby aims at describing an integrated automatic tissue characterization software system in OCT imaging for real-time high precision analysis of intracoronary tissues. The proposed system can output a pathological coronary artery tissue type without the need for intensively training clinicians. Even with such training, visual interpretation of the coronary artery OCT images can still be prone to errors compared to the system proposed herein. Complete interpretation and manual detection of various pathological lesion tissues may take weeks and even months for clinicians given the diffuse nature of coronary artery disease sequelae, which can postpone the diagnostic process, decision making, and the possibility of accurate personalized treatment strategy for better patient's outcome. The medical industry is thus in need of the system and methods proposed herein.

Tuning of conventional deep learning networks for pathological tissue extraction and classification tasks results in a time-consuming and complex process, which is not desirable in real-time applications. It is this an aim of the proposed model to be as simple and efficient as possible.

Convolutional neural networks demonstrated strong tissue features to describe various tissues in medical applications. However, conventional CNNs used as classification engines are generally patch-based, which may not be efficient for a number of reasons, including: high computational burden caused by overlapped patches and redundant feature extraction; too many pre-processing steps are required to remove unwanted information in coronary artery OCT images for reducing the computational complexity, which can result in extra computational time and loss of important tissue information in that processing; and patch-size selection can be tricky considering the pooling steps in designing deep networks.

Pixel-wise segmentation using fully convolutional networks can overcome many limitations of CNNs to be used as classifiers. Multi-class segmentation using fully convolutional networks (FCNs) for plaque characterization may not be desirable. Considering limited dataset in medical applications, training process will be stronger on all the data to detect all atherosclerotic tissues regardless of their types.

This example contributes to: designing a coronary artery pathological tissue characterization model, and more specifically a fully automatic atherosclerotic plaque characterization model. The system described in the following paragraphs accelerates the analysis of coronary artery OCT images by minimizing the computational complexity, and accelerating the model performance by using, for instance, original images without pre-processing. In addition, the proposed system combines advantages arising from using dilated convolutional layers, and from using a sparse auto-encoder for pathological tissue type characterization. The proposed system, due to its architecture, provides fast and accurate training using minimum feature extraction process. In some embodiments, advantages also arise from using a sparse auto-encoder to generate more pathological tissues in the classification process and expand on the existing training data sets.

Figure 7A:
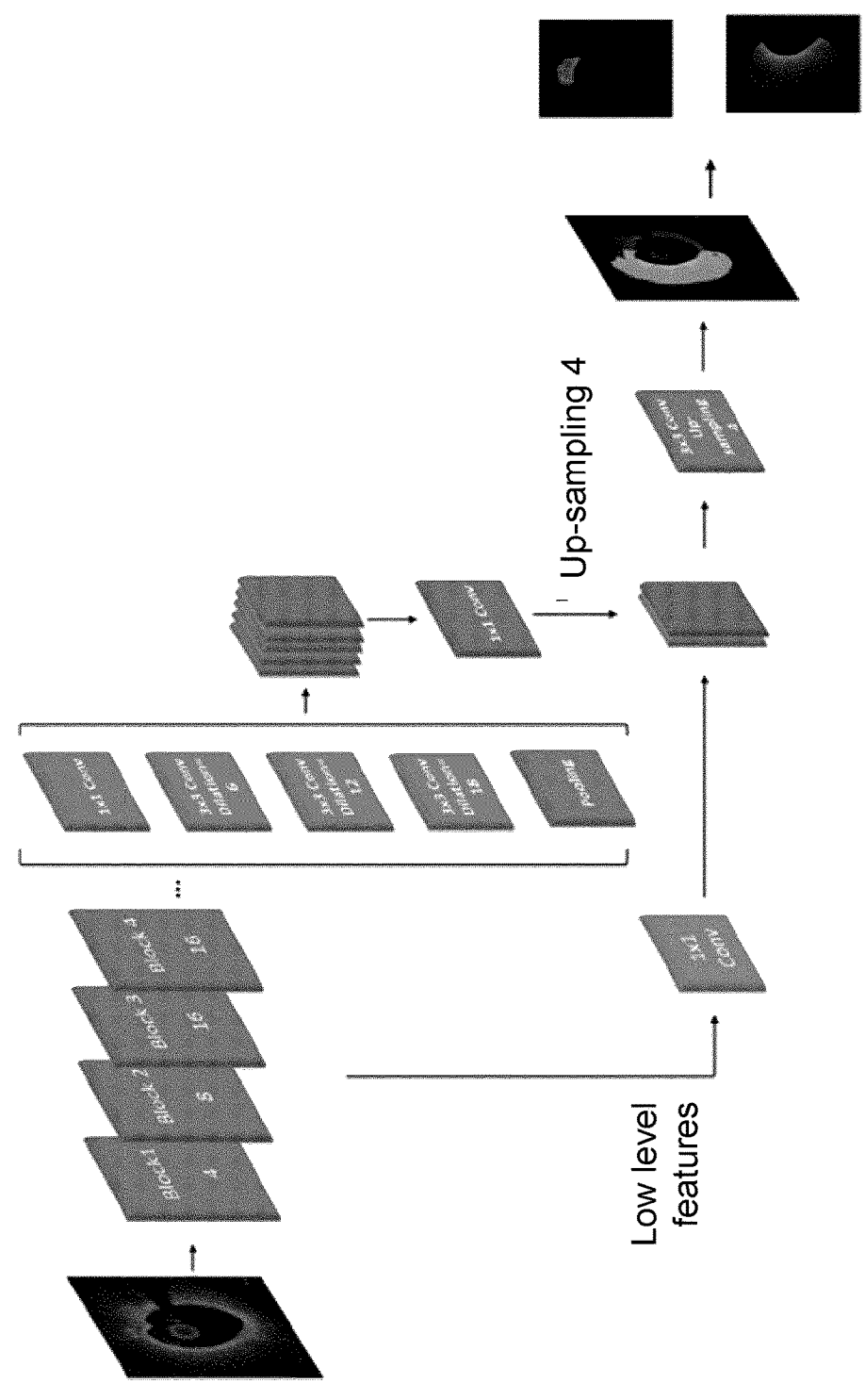
FIG. 7A is a schematic view of an example of a trained fully convolutional engine of another example system for determining a pathological tissue type in a coronary artery OCT image, in accordance with one or more embodiments.
Figure 7B:
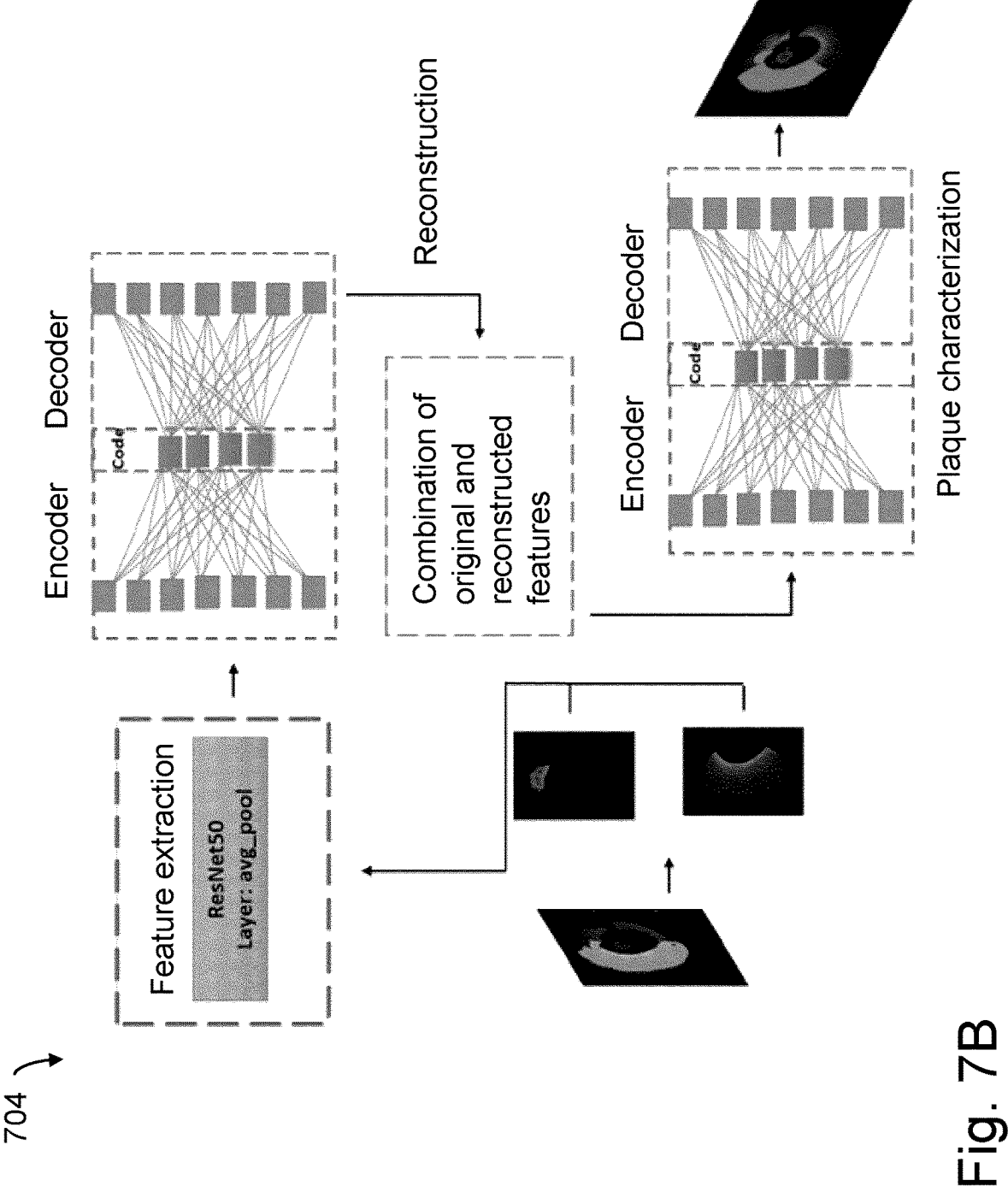
FIG. 7B is a schematic view of an example of a trained auto-encoder classification engine of the system of FIG. 7A, in accordance with one or more embodiments.

The proposed system includes a combination of spatial pyramid pooling module with dilated convolutions is proposed for semantic segmentation to extract all pathological tissues, including atherosclerotic tissues, regardless of their types. Then, a sparse auto-encoder engine is trained on CNN features extracted from various coronary plaques and pathological formations for both feature reconstruction and plaque type characterization. More specifically, FIG. 7A shows an example of a trained fully convolutional engine 702, and FIG. 7B shows an example of a trained auto-encoding classification engine 704.

The proposed system was tested on 41 atherosclerotic OCT pullbacks. Each OCT pullback consists of approximately 200 frames of DICOM images. There are some cases with less than 200 frames per OCT pullback. Image acquisition is performed using FD-OCT (St. Jude Medical Inc., St. Paul, Minnesota, USA) with the pullback speed of 20 mm/sec. The axial and lateral resolutions of the OCT system are 12-15 μm and 20-40 μm respectively. Permission to conduct this study on retrospective OCT studies was granted by the institutional review board. The various atherosclerotic plaques detected in this example include fibrous plaque, fibrocalcific plaque, fibroatheroma with lipid pool/ necrotic core, to name a few examples. Micro-vessels and thrombus were also considered as pathological tissues since they can be assigned to plaque vulnerability.

Figure 8:
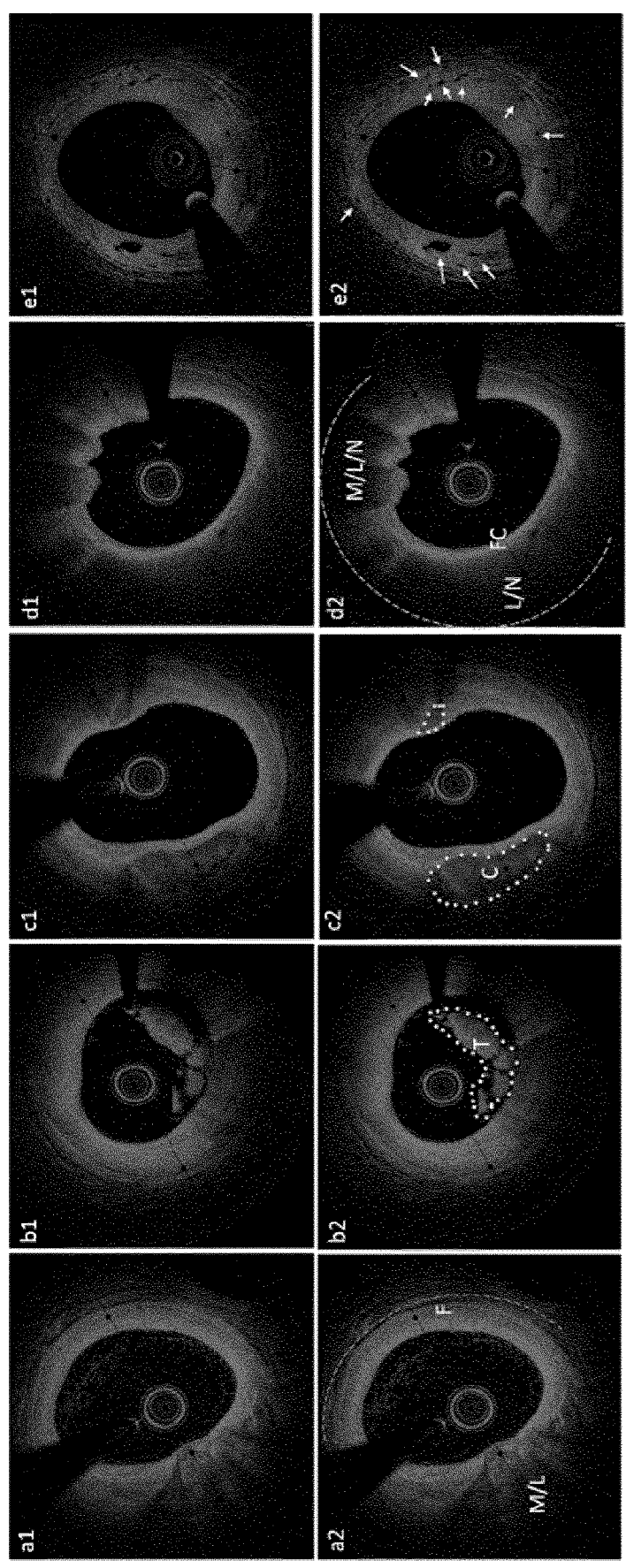
FIG. 8 includes raw, unprocessed coronary artery OCT images and corresponding processed OCT images having annotations showing respective pathological tissue types as determined by trained physician(s), in accordance with one or more embodiments.

Intima is characterized as homogeneous signal-rich layer in OCT images. Media layer is visualized as a signal-poor layer with internal and external elastic lamina as signal-rich bands in OCT images. Macrophages are shown by OCT as signal-rich bright bands or spots with a dorsal shadow in the direction of the light, as shown at insets a1 and d1 of FIG. 8, whereas micro-vessels are visualized as rounded signal-poor structures, as shown at inset e1 of FIG. 8. Fibrous plaque can be represented as a thick signal rich layer followed by media destruction and small area (<1 quadrant) of lipid pool and probable macrophage accumulation, as shown in inset a1 of FIG. 8. Micro-calcification and cholesterol crystals can be seen in fibrous plaques. Fibrocalcific plaque is visualized in OCT images as sharply delineated signal-poor regions, as shown at inset c1 of FIG. 8. Necrotic core is a signal poor region, which is not distinguished by OCT. Therefore, lipid pool/necrotic core, which takes >1 quadrant of the arterial cross-section is visualized as a signal poor region and is considered as the main characteristic of fibroatheroma, as shown at inset d1 of FIG. 8. White and red thrombus are visualized with OCT as homogeneous signal-rich and signal-poor regions, respectively, as shown at inset b1 of FIG. 8. The coronary artery OCT images of insets a1 through e1 of FIG. 8 were labeled by trained operator using a custom software, the result of which is shown at insets a2 through e2 of FIG. 8. Each annotated image was reviewed by two cardiologists and if there was any disagreement, a consensus was reached by reviewing carefully each region of interest.

Figure 9:
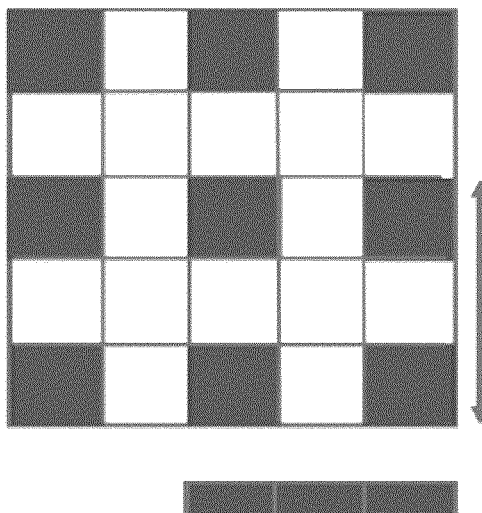
FIG. 9 is a schematic image showing example of conventional and dilated convolutional layers of the trained fully convolutional engine of FIG. 7A with respective dilation rates of 1 and 2, in accordance with one or more embodiments.
Figures 10A, 10B, 10C, 10D:
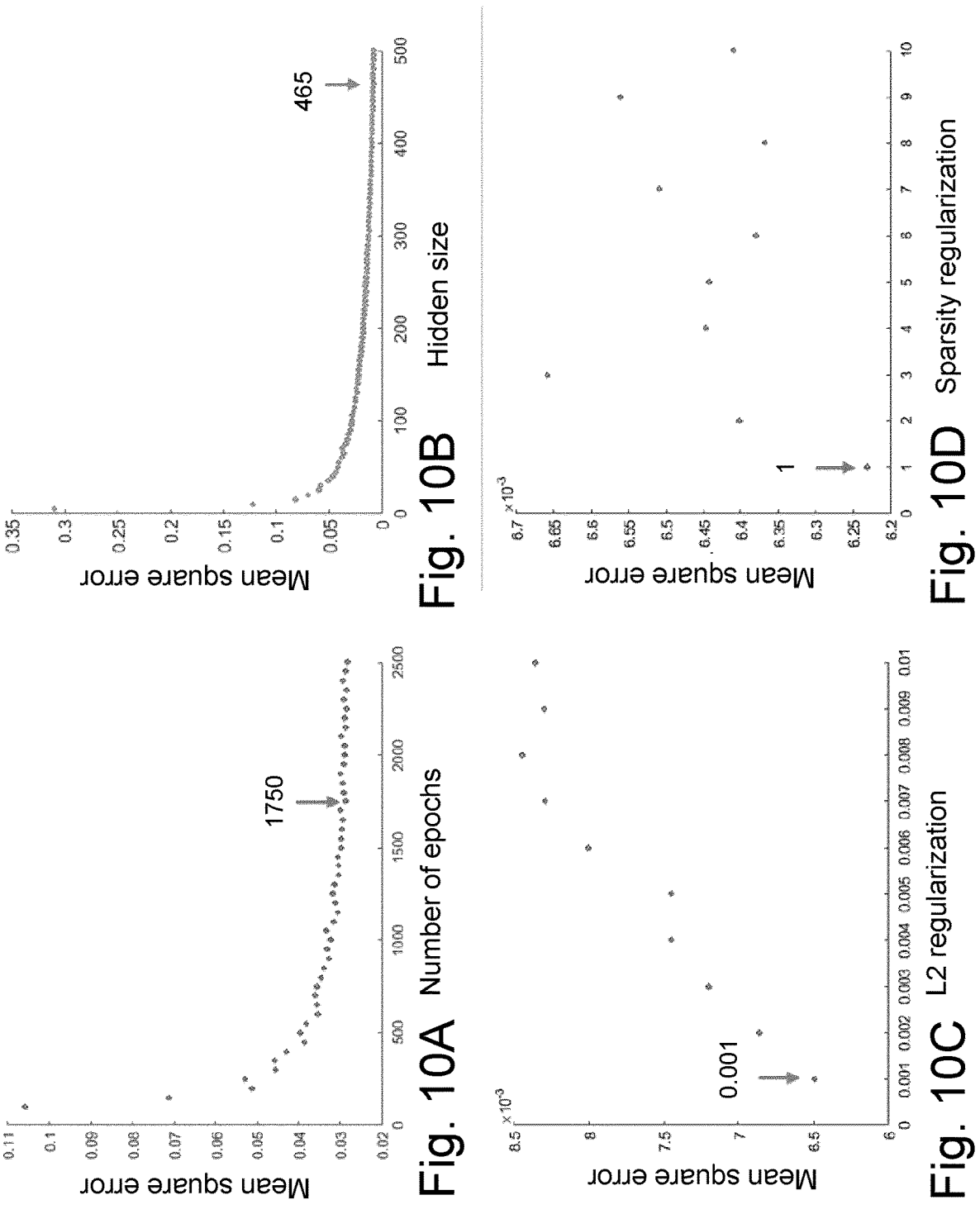
FIG. 10A is a graph showing the mean square error as a function of the number of epochs for the training of the auto-encoder classification engine of FIG. 7B, in accordance with one or more embodiments.
FIG. 10B is a graph showing the mean square error as a function of the hidden size for the training of the auto-encoder classification engine of FIG. 7B, in accordance with one or more embodiments.
FIG. 10C is a graph showing the mean square error as a function of the L2 regularization for the training of the auto-encoder classification engine of FIG. 7B, in accordance with one or more embodiments.
FIG. 10D is a graph showing the mean square error as a function of the sparsity regularization for the training of the auto-encoder classification engine of FIG. 7B, in accordance with one or more embodiments.

Different configurations of FCNs were used for semantic segmentation and object detection in various applications. The models which perform spatial pyramid pooling by applying dilated convolutions demonstrated promising performances. It was found that employing deep convolutional neural networks with dilated convolutions results in faster and stronger encoder-decoder architecture compared against conventional VGG-based FCN. The advantages of both networks were taken into account in the development of an appropriate fully convolutional engine for intracoronary OCT images. Using dilated convolution results in extraction of dense feature maps, which are considerably smaller than the input resolution. This can accelerate the training process. As discussed above, dilated convolutions assign an additional parameter called dilation rate $r_d$ to the convolutional layers. Therefore, compared against standard convolutions (which are characterized by a unitary dilation rate $r_d=0$), the stride, number of parameters, and computational cost maintain constant while the field of view is expanded. This can result in denser output feature maps, which can thereby improve the segmentation performance, such as shown in FIG. 9. As depicted, the convolutional layer shown on the left-hand side has a unitary dilation rate whereas the convolution layer shown on the right-hand side has a dilation rate greater than one, thereby yielding a dilated convolutional layer. For each network, at each layer, some filters (kernels) may be defined to move on the OCT image and extract features from different regions of interest of the OCT image. As such, it is noted that it is actually the kernel or filter which is moving on the OCT image with a dilation rate to increase the field of view by keeping the computational time, number of parameters, and stride constant. In other words, instead using large filters with more parameters to have a larger field of view and get more information from the image, small filters with dilation rates greater than the unity are used to expedite the computations. This way, the same number of parameters are kept as when using conventionally small filters, but a larger field of view and denser feature maps are obtained without increasing the computational burden. Using dilated convolution, it is noted that:

$$y[i]=\Sigma_k x[i+r \cdot k]w(k), \tag{1}$$

where i is a location in output y. As such, a dilated convolution with dilation rate i is applied over feature map x with kernel w. Resnet-based encoder with dilated convolutions is applied in this example. In this aspect, instead of using large kernels, smaller kernels and specific dilation rate can cover a wide field of view as large kernels but using the same number of parameters as small kernels. This can avoid learning extra parameters while it results in denser output feature maps to develop strong network with fast performance.

To find the optimal learning parameters, extensive range of values were considered for each parameter and the performance of the network was evaluated on validation set. It was found that assigning a learning rate of 0.01 results in optimal performance of the network. Dilation rates of 2 and 4 were applied to the last two blocks for output stride of 8 to obtain denser feature map and thereby improve the network segmentation performance. Decoder up-samples the encoder output by up-sampling factor of 8 and combine them with corresponding low level features after applying 1×1 convolution. The last step is to refine the features using 3×3 convolutions for final segmentation result. Various atherosclerotic tissues illustrate a small fraction of the image considering the background and other surrounding tissues. Therefore, to deal with the class-imbalanced problem, a weighted cross-entropy was used, with a weight defined as follows:

$$w=N-(\Sigma_n p_n/\Sigma_n p_n), \tag{2}$$

where N is the number of images annotated as foreground with predicted probabilistic map elements $p_n$.

To start training the model, 80% of the images from all the pullbacks were considered as training set, and the rest 20% was divided by two to be considered as validation and test sets. Leave-one-out cross-validation was performed to evaluate the performance of the model on various settings of training, validation, and test sets and assure that the model can be generalized. At each step, one pullback was left out as validation set, and to train the model on other remaining pullbacks.

The auto-encoding classification engine is a neural network with the same structure as the multi-layer perceptron. Such Autoencoders can investigate the attributes that can properly represent and reconstruct the input data. This can prevent over-fitting due to insufficient annotated data. In this example, a sparse auto-encoding classification engine was trained, with an additional parameter of sparsity regularization to enforce a constraint on the sparsity of the output from the hidden layer. The input data is mapped by encoder into the code, which is generated by the hidden layer. Then, decoder maps the code to reconstruct the input data. As the first step, the sparse auto-encoding classification engine was trained to generate more input data. Since deep features can represent detailed information of coronary tissues accurately, to accelerate the process of auto-encoder training, Resnet50 was applied as feature extractor. The extracted deep features is used as the input data to train the sparse auto-encoding classification engine with mean square error as the loss function, L2 regularization of 0.001 with sparsity regularization, and sparsity proportion of 1 and 0.05 respectively. Training was performed for 1750 epochs in this example. Optimal value of each parameter is selected through grid searching for various range of values by evaluating the model performance at each step of grid searching, as more detailed in the graphs of FIGS. 10A through 10D. It was demonstrated that the best performance as neural transfer can function for both encoder and decoder. The reconstructed feature map is evaluated by measuring the mean square error between the input deep features and reconstructed features. In second step, the reconstructed features and the original features were combined to expand on the training data for pathological tissue type determination, and more specifically for plaque type characterization. A softmax layer was trained to classify atherosclerotic plaque types including fibrous plaque, fibrocalcific plaque, and fibroatheroma and other pathological formations including micro-vessel, and thrombus since they are important factors in coronary plaque vulnerability. Then, the encoder of the auto-encoding classification engine was stacked with the softmax layer to build a stacked network for classification task. It should be noticed that although the training of the auto-encoding classification engine is unsupervised, training the softmax layer can be supervised using the training data labels at a subsequent step. The total input data was divided into three sets of 70% for training, 15% for validation, and the remaining 15% for test. Leave-one-out cross-validation was performed to assure the model can be generalized to all possible selections of training, validation, and test sets.

As the first step of atherosclerotic coronary analysis, all the atherosclerotic tissues including plaques and other pathological formations were extracted using a spatial pyramid pooling module with dilated convolutions to build an encoder-decoder network for foreground/background segmentation, as discussed above. All atherosclerotic tissues are annotated as foreground. Image background and other tissues are labeled as background. The results are shown in Table 1. Measured accuracy, specificity, sensitivity, and BF-score demonstrate the good performance of the model to extract all atherosclerotic tissues regardless their types.

TABLE 1

| Measured accuracy, sensitivity, specificity, and BF-score for detecting the plaques and pathological formations regardless their types. | | | | |
|---|---|---|---|---|
| Tissues under review | accuracy | sensitivity | specificity | BF-Score |
| Atherosclerotic tissues | 0.93 ± 0.10 | 0.90 ± 0.13 | 0.95 ± 0.07 | 0.84 ± 0.18 |

Figure 11:
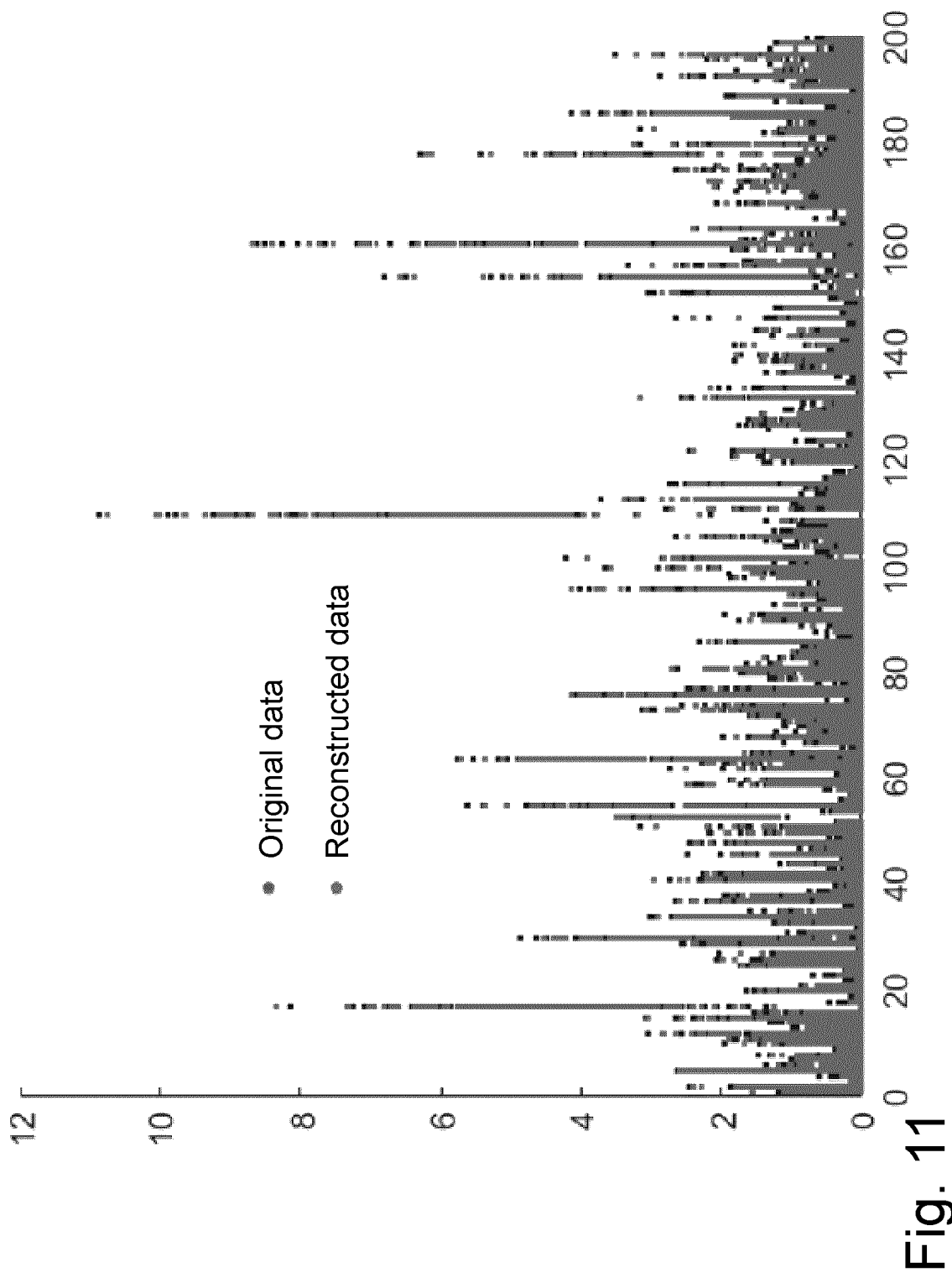
FIG. 11 is a graph showing overlapping between the original and reconstructed features, in accordance with one or more embodiments.
Figure 12:
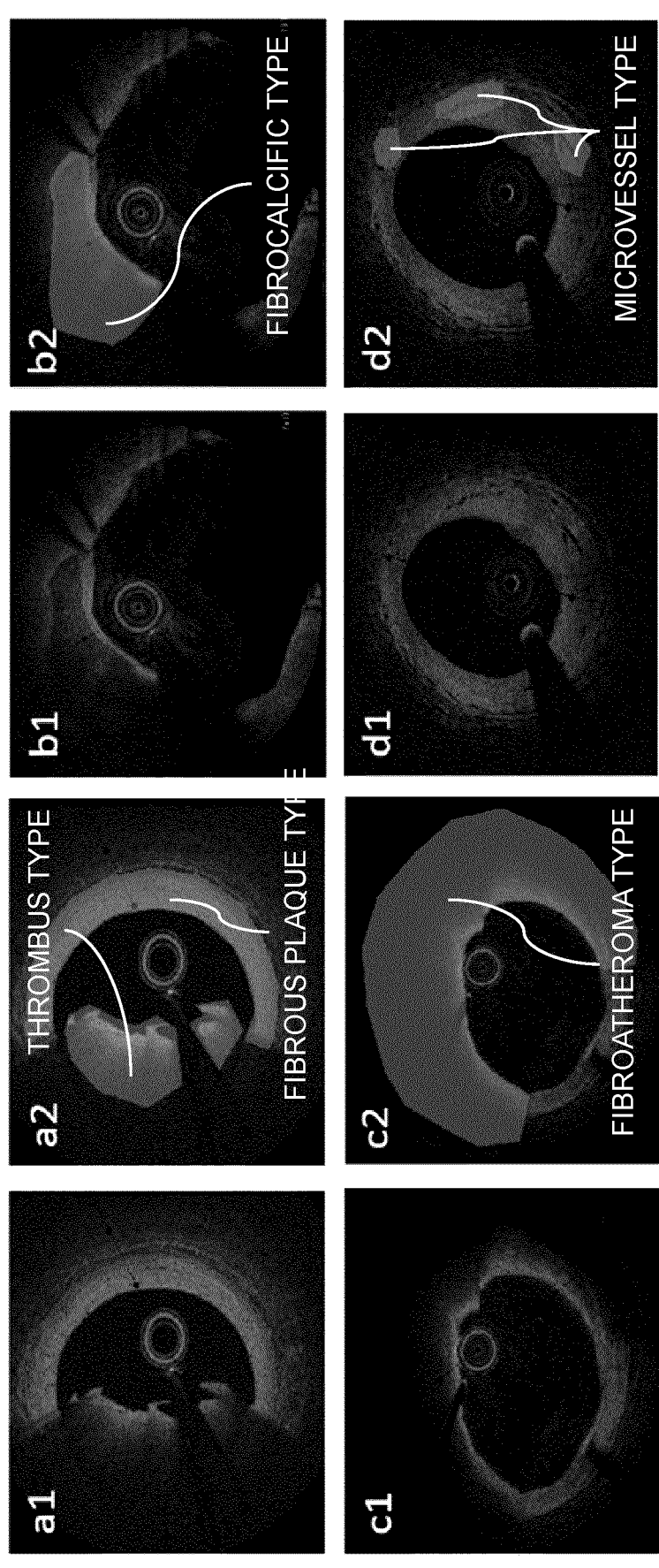
FIG. 12 includes raw, unprocessed coronary artery OCT images and corresponding processed OCT images having annotations showing respective pathological tissue types as determined by the trained engines of FIGS. 7A and 7B, in accordance with one or more embodiments.

The next step was to train sparse autoencoders for the following reasons: feature reconstruction; and atherosclerotic tissue type characterization. Using deep features, training the autoencoder is very fast with accurate performance. Deep features were extracted from various plaques as input of the sparse autoencoder. The mean square error measured between the original input features and reconstructed features is 0.006. The overlap between the original and reconstructed features is shown in FIG. 11 for small portion of the data. For plaque classification including fibrous plaque, fibrocalcific, and fibroatheroma as well as other pathological formations such as thrombus and micro-vessel, a softmax layer is trained in 1000 epochs. Per-class classification results shown in Table 2 demonstrate the high performance of the model. Visual representation of the atherosclerotic tissue characterization model proposed in this study is shown in FIG. 12. More specifically, FIG. 12 emphasizes atherosclerotic tissue characterization, with insets a1 through d1 showing raw, unprocessed coronary artery OCT images. Inset a2 of FIG. 12 identifies a region encompassing a thrombus type of pathological tissue, and a region encompassing a fibrous plaque type of pathological tissue; inset b2 of FIG. 12 identifies a region encompassing a fibrocalcific type of pathological tissue; inset c2 identifies fibroatheroma type of pathological tissue, with lipid pool/necrotic core; and inset d2 identifies a micro-vessel type of pathological tissue. It is noted that the proposed system processed the original OCT images and, using the trained engines described herein, outputted the pathological tissue types as a text overlay on the original OCT images for ease of review.

TABLE 2

| Measured accuracy, sensitivity, specificity, for plaque type characterization | | | |
|---|---|---|---|
| Atherosclerotic tissues | accuracy | sensitivity | specificity |
| Fibrous plaque | 0.99 | 0.99 | 1.00 |
| Fibrocalcific | 0.96 | 0.96 | 0.97 |
| Fibroatheroma | 0.98 | 0.98 | 0.98 |
| Thrombus | 0.99 | 0.98 | 0.99 |
| Micro-vessel | 0.84 | 0.74 | 0.98 |

It is noted that the systems and methods described herein can be configured to generating an output image having the atherosclerotic pathological tissue type overlaid over said OCT image, with a lead line leading to the region of interest. Examples of such output images are shown in FIG. 12. In some embodiments, the methods and systems are configured to associate a tag indicative of unhealthiness to the OCT image upon finding at least one atherosclerotic pathological tissue type in the OCT image. Other tags, such as healthy tags, can also be associated if no atherosclerotic pathological tissue type is found in the OCT image, for instance.

As discussed above, the system proposed herein is designed to be applicable in real-time analysis of tissues under review. Therefore, not only the models perform precisely, but they are also fast with reduced computational complexity as much as possible. The proposed system aims at solving challenges from conventional systems. More specifically, the proposed system considers the pathological tissues, and more specifically the atherosclerotic tissues. In this example, it was shown that significant determinants of plaque vulnerability such as micro-vessels, thrombus, and fibroatheroma with macrophage infiltration and lipid pool/necrotic core formation can be identified using trained engines. The system includes an encoder-decoder with dilated convolutions to extract all atherosclerotic tissues regardless their type, and sparse autoencoders on deep features for either feature reconstruction and atherosclerotic tissue type characterization. As a result, it was shown that computational complexity can be reduced compared to conventional techniques.

As can be understood, the examples described above and illustrated are intended to be exemplary only. The scope is indicated by the appended claims.

What is claimed is:

1. A system for determining an atherosclerotic pathological tissue type of a coronary artery, the system comprising:
an optical coherence tomography (OCT) imaging system being configured for acquiring an OCT image of tissue within said coronary artery; and
a controller having a processor and a memory having instructions stored thereon that when executed by said processor perform the steps of:
using a trained fully convolutional engine stored on said memory and having a plurality of convolutional layers with respective dilation rates different than unity, extracting a plurality of pathological tissues regardless their type in at least a region of interest of said OCT image;
using a trained auto-encoder classification engine stored on said memory and having a layer characterized with a sparsity regularization parameter, determining an atherosclerotic pathological tissue type associated to said region of interest of said OCT image based on said extracted pathological tissues; and
outputting said atherosclerotic pathological tissue type of said coronary artery.

2. The system of claim 1 wherein said atherosclerotic pathological tissue type is selected from the group consisting of: fibrous plaque, fibrocalcific, fibroatheroma, acute thrombus, and micro-vessels.

3. The system of claim 1 wherein at least one of said dilation rates is greater than a dilation rate threshold.

4. The system of claim 3 wherein said dilation rate threshold is the unity.

5. The system of claim 1 wherein the layer of the auto-encoder classification engine is a hidden layer.

6. The system of claim 1 wherein said sparsity regularization parameter ranges within a given sparsity regularization parameter range.

7. The system of claim 1 wherein said outputting includes generating an output image having the atherosclerotic pathological tissue type overlaid over said OCT image, with a lead line leading to the region of interest.

8. The system of claim 1 wherein upon finding at least one atherosclerotic pathological tissue type in said OCT image, associating a tag indicative of unhealthiness to the OCT image.

9. A method for determining an atherosclerotic pathological tissue type of a coronary artery, the method comprising:
using an optical coherence tomography (OCT) imaging system, acquiring an OCT image of tissue within said coronary artery;
using a controller,
using a trained fully convolutional engine stored on a memory of said controller and having a plurality of convolutional layers with respective dilation rates, extracting a plurality of pathological tissues regardless their type in at least a region of interest of said OCT image;
using a trained auto-encoder classification engine stored on said memory and having a layer characterized with a sparsity regularization parameter, determining an atherosclerotic pathological tissue type associated to said region of interest of said OCT image based on said extracted pathological tissues; and
outputting said atherosclerotic pathological tissue type of said coronary artery.

10. The method of claim 9 wherein said atherosclerotic pathological tissue type is selected from the group consisting of: fibrous plaque, fibrocalcific, fibroatheroma, acute thrombus, and micro-vessels.

11. The method of claim 9 wherein at least one of said dilation rates is greater than a dilation rate threshold.

12. The method of claim 11 wherein said dilation rate threshold is the unity.

13. The method of claim 9 wherein the layer of the auto-encoder classification engine is a hidden layer.

14. The method of claim 9 wherein said sparsity regularization parameter ranges within a given sparsity regularization parameter range.

15. The method of claim 7 wherein said outputting includes generating an output image having the atherosclerotic pathological tissue type overlaid over said OCT image, with a lead line leading to the region of interest.

16. The method of claim 7 wherein upon finding at least one atherosclerotic pathological tissue type in said OCT image, associating a tag indicative of unhealthiness to the OCT image.

* * * * *